US012700484B2

(12) United States Patent
Kim et al.

(10) Patent No.: US 12,700,484 B2
(45) Date of Patent: Aug. 4, 2026

(54) NAMED-ENTITY RECOGNITION OF PROTECTED HEALTH INFORMATION

(71) Applicant: Palo Alto Networks, Inc., Santa Clara, CA (US)

(72) Inventors: Jesse Mie Kim, Palo Alto, CA (US); Ashwin Kumar Kannan, San Francisco, CA (US); Anirudh Mittal, Fremont, CA (US); William Redington Hewlett, II, Mountain View, CA (US); Naresh Kumar Venkata Guntupalli, Fremont, CA (US)

(73) Assignee: Palo Alto Networks, Inc., Santa Clara, CA (US)

( * ) Notice: Subject to any disclaimer, the term of this patent is extended or adjusted under 35 U.S.C. 154(b) by 401 days.

(21) Appl. No.: 18/191,546

(22) Filed: Mar. 28, 2023

(65) Prior Publication Data

US 2024/0331815 A1     Oct. 3, 2024

(51) Int. Cl.
| | |
|---|---|
| *G16H 10/60* | (2018.01) |
| *G06F 40/279* | (2020.01) |
| *G06F 40/295* | (2020.01) |
| *G06N 3/045* | (2023.01) |
| *G06N 3/09* | (2023.01) |
| *G06N 5/01* | (2023.01) |
| *G06N 20/20* | (2019.01) |

(52) U.S. Cl.
CPC ........... *G16H 10/60* (2018.01); *G06F 40/279* (2020.01); *G06N 3/045* (2023.01); *G06N 3/09* (2023.01)

(58) Field of Classification Search
CPC ..... G16H 10/60; G06F 40/279; G06F 40/295; G06N 3/045; G06N 3/09; G06N 5/01; G06N 20/20
See application file for complete search history.

(56) References Cited

U.S. PATENT DOCUMENTS

| | | | | |
|---|---|---|---|---|
| 10,970,488 | B2 * | 4/2021 | Muraoka | G06F 40/30 |
| 11,797,705 | B1 * | 10/2023 | Voinea | G06F 21/6245 |
| 2022/0138534 | A1 * | 5/2022 | Veyseh | G06F 40/30 |
| | | | | 706/15 |
| 2023/0125785 | A1 * | 4/2023 | Master | G06F 40/30 |
| | | | | 704/9 |

OTHER PUBLICATIONS

"NeuroNER", [online], [retrieved on Mar. 31, 2023] Retrieved from the Internet: <http://neuroner.com/>.

(Continued)

*Primary Examiner* — Hai Phan
*Assistant Examiner* — Ian Scott Mclean
(74) *Attorney, Agent, or Firm* — Gilliam IP PLLC

(57) ABSTRACT

A named-entity recognition (NER) model detects named entities with types that correspond to protected health information (PHI) in potentially sensitive documents. The NER model is trained to detect named entities corresponding to both personally identifiable information (PII) and medical terms. Output of the NER model is preprocessed as input to a random forest classifier that outputs a verdict that documents comprise sensitive data. The verdict is interpretable via high confidence named entities detected by the NER model that led to the verdict.

20 Claims, 5 Drawing Sheets

(56)     References Cited

OTHER PUBLICATIONS

"Robust DeID: De-Identification of Medical Notes using Trans-former Architectures", [online], [retrieved on Mar. 31, 2023] Retrieved from the Internet: <https://github.com/obi-ml-public/ehr_deidentification>.

Norgeot, et al., "Protected Health Information filter (Philter): accu-rately and securely de-identifying free-text clinical notes", npj Digital Medicine vol. 3, Article No. 57, Apr. 14, 2020, 8 pages.

Patel, "BioNerFlair: biomedical named entity recognition using flair embedding and sequence tagger", [online], [retrieved on Mar. 31, 2023] Retrieved from the Internet: <https://arxiv.org/pdf/2011.01504.pdf>.

Speck, et al., "Ensemble Learning for Named Entity Recognition", The Semantic Web—ISWC 2014. ISWC 2014. Lecture Notes in Computer Science, vol. 8796. Springer, Cham., Oct. 19, 2014,16 pages.

Trienes, et al., "Comparing Rule-based, Feature-based and Deep Neural Methods for De-identification of Dutch Medical Records", Proceedings of the 1st ACM WSDM Health Search and Data Mining Workshop (HSDM2020), arXiv:2001.05714.

Yang, et al., "Automatic Detection of Protected Health Information from Clinic Narratives", J Biomed Inform. Dec. 2015; 58 (Suppl): S30-S38, 25 pages. doi: 10.1016/j.jbi.2015.06.015.

* cited by examiner

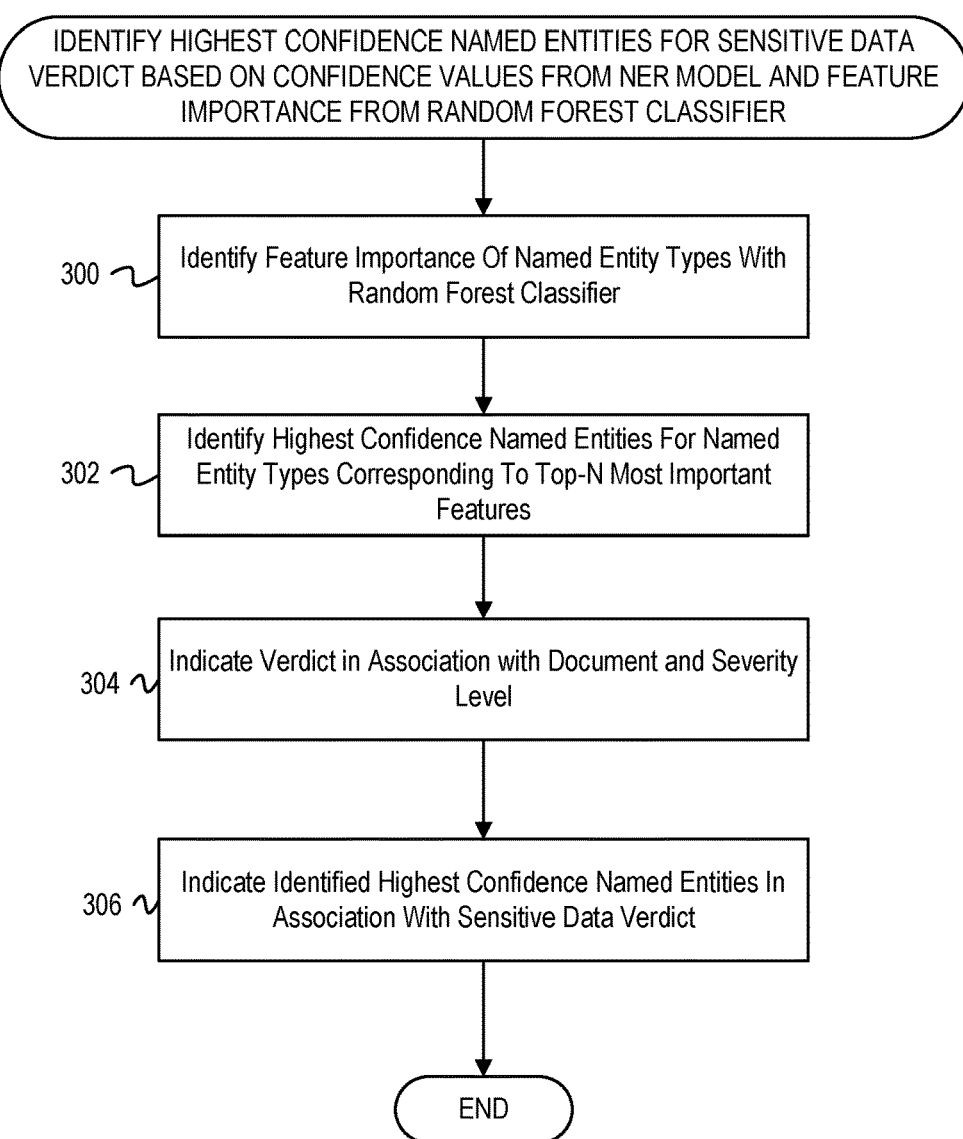

IDENTIFY HIGHEST CONFIDENCE NAMED ENTITIES FOR SENSITIVE DATA VERDICT BASED ON CONFIDENCE VALUES FROM NER MODEL AND FEATURE IMPORTANCE FROM RANDOM FOREST CLASSIFIER

300 — Identify Feature Importance Of Named Entity Types With Random Forest Classifier 302 — Identify Highest Confidence Named Entities For Named Entity Types Corresponding To Top-N Most Important Features 304 — Indicate Verdict in Association with Document and Severity Level 306 — Indicate Identified Highest Confidence Named Entities In Association With Sensitive Data Verdict

END

FIG. 3

NAMED-ENTITY RECOGNITION OF PROTECTED HEALTH INFORMATION

BACKGROUND

The disclosure generally relates to G06F 21/62 and subclass G06 21/6245.

Data loss prevention is a security measure for detecting and handling documents that comprise sensitive data. Sensitive data can comprise user information, financial information, passwords, medical information, and other compromising types of data. One type of sensitive data is protected health information (PHI), i.e., patient information protected under U.S. law. PHI relates to anything about a patient's medical record or payment history.

Named-entity recognition (NER) is a natural language task that identifies and assigns types to named entities in documents. Natural language models for NER include neural networks with natural language processing architecture and vary from unsupervised to semi-supervised models. Natural language models trained for other natural language understanding tasks are often adapted to the context of NER.

BRIEF DESCRIPTION OF THE DRAWINGS

Embodiments of the disclosure may be better understood by referencing the accompanying drawings.

FIG. 3 is a flowchart of example operations for identifying decisions in a random forest classifier that determined that the document comprises sensitive data.

DESCRIPTION

Figure 1:
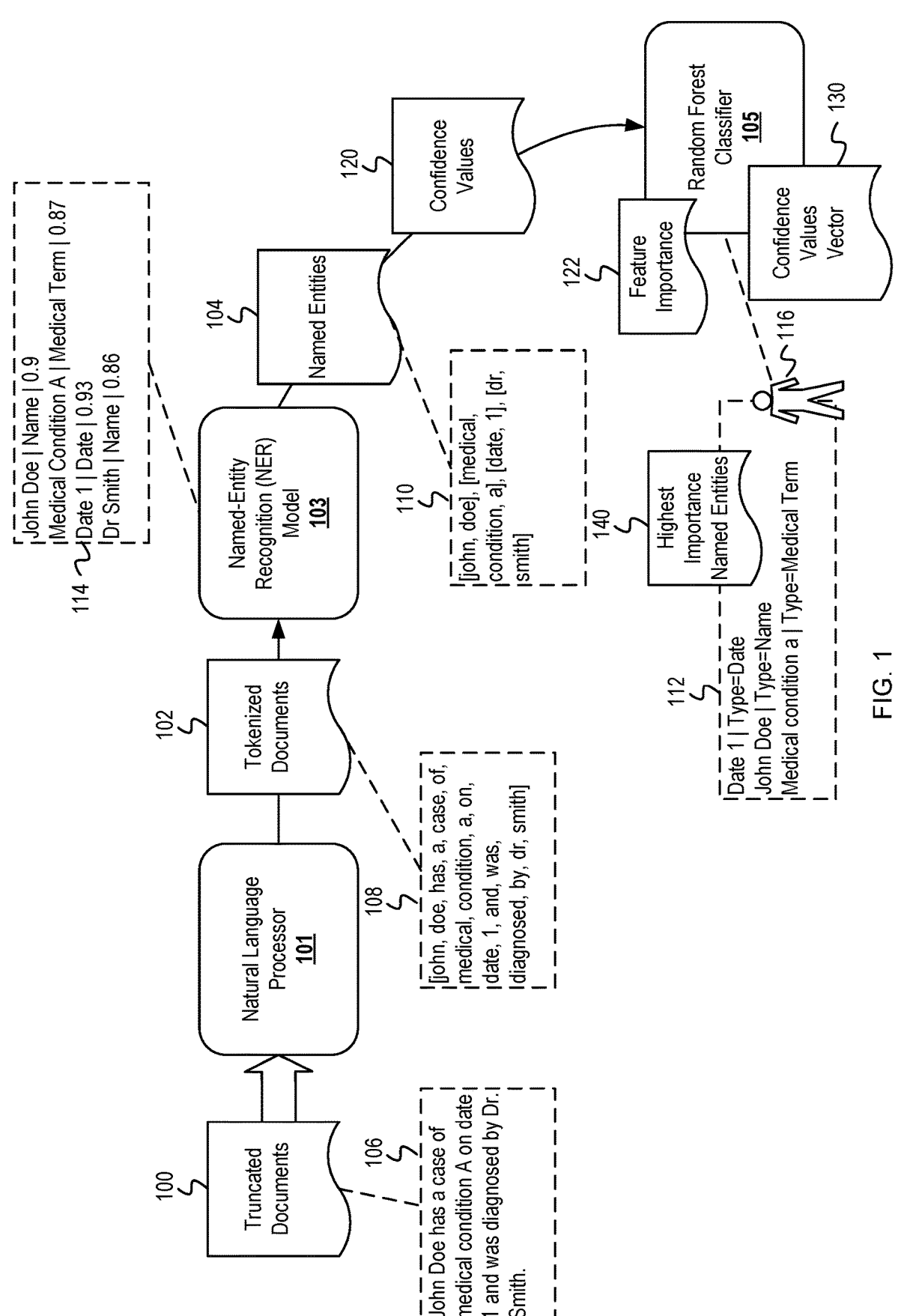
FIG. 1 is a schematic diagram of an example system for detecting PHI in a document with a NER model and a random forest classifier.

The description that follows includes example systems, methods, techniques, and program flows to aid in understanding the disclosure and not to limit claim scope. Well-known instruction instances, protocols, structures, and techniques have not been shown in detail for conciseness.

Overview

Existing models for detecting PHI for data loss prevention fail to incorporate both medical terms and personally identifiable information (PII). This results in failure to predict specific combinations of medical terms and PII that strongly correlate with PHI in a document. Often, PHI will involve both PII and medical terms, for instance when documents specify medical conditions in association with patient information. A named-entity recognition (NER) model is disclosed herein to identify named entities for both PII and medical terms. Types of named entities that take values in PII and medical terms (e.g., people, phone numbers, medical terminology, etc.) also occur outside of the context of PHI, and the NER model is first trained for named entity recognition on general context named entities and then further trained in the context of PII and medical terms. A natural language processor truncates/subdivides and tokenizes documents before the documents are input to the NER model to identify named entities as possible indicators of PHI in the documents and confidence values that indicate the confidence that each named entity has a correct entity label. For each type of named entity for PII and medical terms, mean and maximal confidence values for named entities of that type are concatenated into vectors of confidence values. A random forest classifier trained on these vectors of confidence values predicts whether the documents contain PHI.

Use of a random forest classifier allows for determining relative importance of named entity types that resulted in a verdict that a document comprises sensitive data. The random forest classifier identifies highest confidence named entities in the document with named entity types indicated as high importance. This results in a list of named entities with the document that are explanatory of the sensitive data verdict. The combination of the NER model and random forest classifier ensures robust detection of named entities across both PII and medical terms and interpretable PHI detection.

Terminology

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

The term "document" as used herein refers to any structured or unstructured text stored in a file or otherwise extracted (e.g., using optical character recognition) for further analysis and data loss prevention. Documents can vary in length and format.

Example Illustrations

FIG. 1 is a schematic diagram of an example system for detecting PHI in a document with a NER model and a random forest classifier. A natural language processor 101 receives truncated documents 100 processed by a natural language processing component not depicted in FIG. 1, wherein the truncated documents 100 comprise fixed-length truncations of a document for efficient processing by subsequent models. The document that was truncated to generate the truncated documents 100 comprises a document with potentially sensitive PHI for data loss prevention. The document may have been detected by a firewall, for instance using optical character recognition. The natural language processor 101 tokenizes the truncated documents 100 to generate tokenized documents 102. A NER model 103 receives the tokenized documents 102 and detects named entities 104 that comprise sequences of tokens in the tokenized documents 102 and confidence values 120 that each of the named entities 104 is the corresponding entity. A random forest classifier 105 vectorizes the confidence values 120 and predicts whether the truncated documents 100 comprise sensitive PHI.

An example truncated document 106 comprises the following text: John Doe has a case of medical condition A on date 1 and was diagnosed by Dr. Smith. The example truncated document 106 comprises PHI including a patient name "John Doe", a medical term "medical condition A", a date "date 1", and a diagnosing physician "Dr. Smith." An example tokenized document 108 comprises the following vector of tokens:

[john, doe, has, a, case, of, medical, condition, a, on, date, 1, and, was, diagnosed, by, dr, smith]

Note that each of the tokens are normalized to be lowercase and separated by white spaces. Other preprocessing steps such as removal of specified ranges of American Standard Code for Information Interchange (ASCII) characters can be implemented by the natural language processor 101.

The NER model 103 receives the tokenized documents 102 and identifies named entities 104 and confidence values 120 for each of the named entities 104 that indicate confidence for each predicted named entity. The named entities 104 comprise sequences of tokens from the tokenized documents 102 such as example named entities 110:

[john, doe], [medical, condition, a], [date, 1], [dr, smith]

Example confidence values and labels 114 for the example named entities 110 comprise the following:

John Doe|Name|0.9

Medical Condition A|Medical Term|0.87

Date 1|Date|0.93

Dr Smith|Name|0.86

The NER model 103 is trained to detect types of named entities specific to PII and medical terms such as "Name" and "Date" for PII and "Medical Term" for medical terms in the above example. For instance, the NER model 103 can be a Bidirectional Encoder Representations from Transformers (BERT) model. The BERT model is trained on billions of tokens for named entity recognition or other natural language tasks and can be further trained on named entities specific to PHI and medical terms such as the foregoing categories of named entities. For efficiency in training and deployment, the NER model 103 can instead be a Distil-BERT model. BERT and DistilBERT models are trained on general language tasks such as masked language modeling and next sentence prediction and modified for NER by, for instance, modifying input layers and classifier heads.

The random forest classifier 105 vectorizes the confidence values 120 per-type of named entity. For instance, the random forest classifier 105 can determine a maximal and a mean confidence value for each type of named entity in the named entities 104 and can generate a vector of confidence values 130 with each entry corresponding to a maximal or mean confidence value for a particular named entity type. Other vectorizations for the confidence values 120 including entries for minimal confidence values, median confidence values, etc. can be used. Entries of the vector of confidence values 130 for types of named entities not present in the named entities 104 can be set to 0, i.e., the vector of confidence values 130 is initialized to zeroes. The random forest classifier 105 determines whether the truncated documents 100 comprise sensitive data according to a consensus of verdicts across each tree in the forest based on inputting the vector of confidence values 130.

For a sensitive data verdict, the random forest classifier 105 determines feature importance 122 for named entity types in the named entities 104 that determined the truncated documents 100. Each important feature indicated by the feature importance 122 corresponds to an input to the random forest classifier 105, i.e., an entry in the vector of confidence values 130 and, thus, to a type of named entity. The random forest classifier 105 determines highest confidence named entities in the named entities 104 with types indicated as highest importance in the feature importance 122 and highest confidence values in the confidence values 120 among named entities with same respective types to generate a list of highest confidence named entities 140 displayed in a user interface of a user 116. Example list of highest confidence named entities 112 comprises named entity "date 1" of type date, named entity "John Doe" of type name, and named entity "medical condition a" of type medical term.

The random forest classifier 105 and NER model 103 were previously trained by a trainer (not depicted) to detect sensitive documents. The training data comprises documents with known/labeled named entities that are also known to comprise sensitive or non-sensitive data. The NER model 103 is trained to identify named entities and their types based on the labels of the named entities. The random forest classifier 105 is trained on training documents that have been preprocessed with the trained NER model 103 and along with their corresponding sensitive/non-sensitive labels. Training occurs according to model type and architecture and can occur across epochs and batches of training data until training criteria are satisfied.

Figure 2:
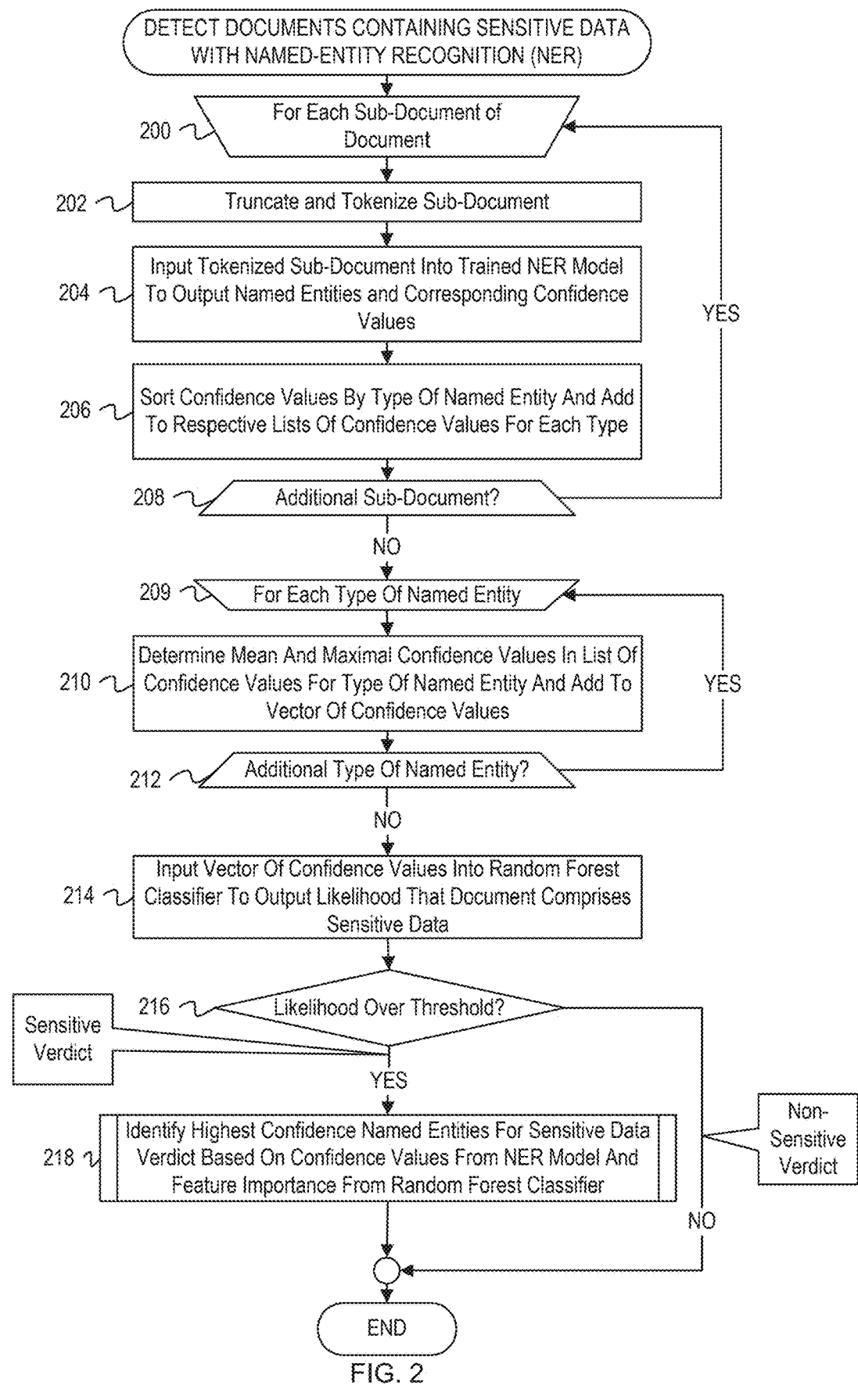
FIG. 2 is a flowchart of example operations for detecting documents containing sensitive data with NER.
Figure 4:
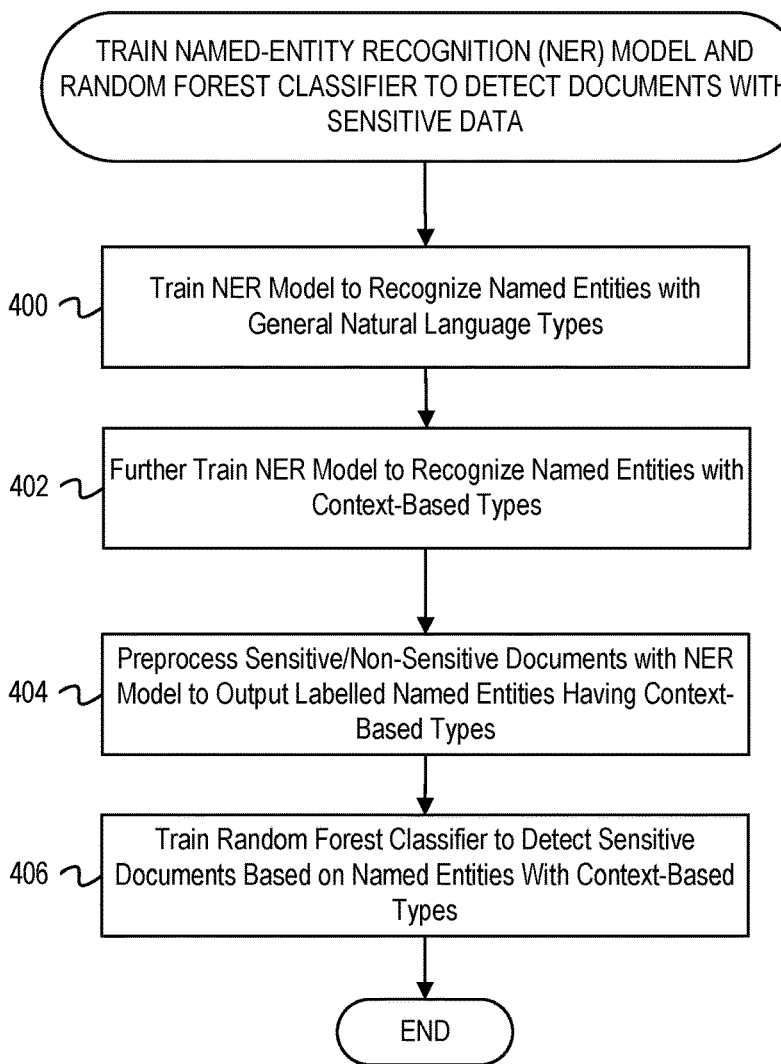
FIG. 4 is a flowchart of example operations for training a NER model and a random forest classifier to detect documents with sensitive data.

FIGS. 2-4 depict flowcharts of example operations for interpretable detection documents with sensitive data with named entity recognition and a random forest classifier. The example operations are described with reference to a natural language processor, a named-entity recognition model, and a random forest classifier, and a trainer for consistency with FIG. 1 and/or ease of understanding. The name chosen for the program code is not to be limiting on the claims. Structure and organization of a program can vary due to platform, programmer/architect preferences, programming language, etc. In addition, names of code units (programs, modules, methods, functions, etc.) can vary for the same reasons and can be arbitrary.

FIG. 2 is a flowchart of example operations for detecting documents containing sensitive data with NER. At block 200, a natural language processor begins iterating through sub-documents of a document. The document comprises potentially sensitive data, for instance PHI, and sub-documents can be delineated according to a fixed truncation length (e.g., 100 kilobytes) that varies depending on available computing resources, types of NER models/classifiers being implemented, etc.

At block 202, the natural language processor truncates and tokenizes the sub-document. The natural language processor truncates the sub-document from the document according to a placeholder indicating a current character of the document comprising the start of the sub-document and a length of each truncated document. For instance, the natural language processor can separate sequences of characters between whitespaces to yield tokens and remove characters within certain ranges of ASCII characters (e.g., non-alphanumeric characters). Other types of natural language processing such as word2vec can be implemented for additional processing of the tokens depending on the type(s) of trained NER models being used. When the trained NER model is a BERT model, the tokens are used as inputs without additional preprocessing.

At block 204, the natural language processor inputs the tokenized sub-document into the trained NER model and obtains outputs comprising named entities and corresponding confidence values. Each named entity comprises a sequence of tokens in the tokenized sub-document with a label of the type of named entity (e.g., name, place, phone number, medical term, etc.). Each confidence value indicates confidence in the label of the type for the corresponding named entity. For instance, the NER model can comprise a BERT model. The BERT model can be trained for general language tasks on millions or billions of tokens and can be further trained in the context of NER for PHI using documents with labels of known named entities for PHI. Other types/architectures of neural networks and types of language models can be implemented.

At block 206, the NER model sorts confidence values by type of named entity and adds the confidence values to lists of confidence values for each type. The NER model sorts the confidence values according to labels indicating each type of named entity. If a list of confidence values has previously been initialized, then the NER model adds confidence values of that type to that list. Otherwise, the NER model initializes a list of confidence values for the corresponding type with the confidence values of that type.

At block 208, the natural language processor continues iterating through sub-documents of the document. If there is an additional sub-document, operational flow returns to block 200. Otherwise, operational flow proceeds to block 209.

At block 209, the NER model begins iterating through types of named entities. The types of named entities comprise named entity types known to correspond to PHI that the NER model was trained to identify. The NER model initializes a vector of confidence values for each of the types as a vector of zeroes that may have a length equal to twice the number of types of named entities.

At block 210, the NER model determines the mean and maximal confidence values in the list of confidence values for the current type of named entity and adds the mean and maximal confidence values to the vector of confidence values. The mean and maximal confidence values are added to the vector of confidence values at entries corresponding to the current type. Additional or alternative values such as minimal confidence values for each type of named entity can be used.

At block 212, the NER model continues iterating through types of named entities. If there is an additional type of named entity, operational flow returns to block 209. Otherwise, operational flow proceeds to block 214.

At block 214, the NER model inputs the vector of confidence values into a random forest classifier to output a likelihood that the document comprises sensitive data. Alternative types of classifiers such as neural networks can be used to generate the likelihood. The random forest classifier determines the likelihood according to a consensus of likelihoods generated from each tree in the random forest classifier.

At block 216, the random forest classifier determines whether the likelihood is over a threshold likelihood. The threshold likelihood can be determined during training to balance precision and recall. If the likelihood is over the threshold likelihood and the verdict of the random forest classifier indicates that the document comprises sensitive data, operational flow proceeds to block 218. Otherwise, the verdict indicates that the document does not comprise sensitive data, and operational flow in FIG. 2 terminates.

At block 218, the random forest classifier identifies highest confidence named entities for the sensitive data verdict based on confidence values from the NER model and feature importance from the random forest classifier. Feature importance for features of the random classifier indicates relative importance of types of named entities. The operations at block 218 are described in greater detail in reference to FIG. 3.

FIG. 3 is a flowchart of example operations for identifying highest confidence named entities for a sensitive data verdict based on confidence values from an NER model and feature importance from a random forest classifier (classifier). The depicted operations occur after the classifier has generated a verdict that the document comprises sensitive data based on named entities detected in the document by a NER model. At block 300, the classifier identifies feature importance of named entity types. The feature importance is a vector of values indicating relative importance of types of named entities for the sensitive data verdict generated based on confidence value inputs to the classifier. Each confidence value corresponds to a type of named entity from which the confidence value was generated (e.g., a maximal or mean confidence value across confidence values for named entities with a type of named entity) and thus the feature importance based on the confidence values indicates relative importance of each type of named entity. The random forest classifier can deduplicate the feature importance by removing types of named entities represented multiple times for multiple confidence values and replacing with the highest importance instance of the named entity.

At block 302, the classifier identifies highest confidence named entities for named entity types corresponding to top-N most important features. The classifier can determine the top-N most important features after deduplicating multiple features for same named entity types. N is a parameter that can be tuned according to a number of named entity types (e.g., N=3). For each of the top-N most important features/named entity types, the classifier identifies named entities in a document corresponding to the sensitive data verdict with highest confidence values obtained from output of the NER model. The classifier stores the highest confidence named entities in a data structure such as a list.

At block 304, the classifier indicates the verdict of sensitive data in association with the document and a severity level. The severity level can be determined according to the highest confidence entities. For instance, each type of named entity can correspond to a severity level and the overall severity level can be the maximal or aggregate severity level for the highest confidence entities in the document. Other rules for determining severity level based on type and frequency of occurrence of named entities can be implemented.

At block 306, the classifier indicates the highest confidence named entities in association with the sensitive data verdict. For instance, the classifier can indicate a list of highest confidence named entities and their types in a user display. The classifier or distinct natural language processing component can extract sentences from the document containing the highest confidence named entities to indicate in the user display.

FIG. 4 is a flowchart of example operations for training a NER model and a random forest classifier to detect documents with sensitive data. At block 400, a model trainer (trainer) trains an NER model to recognize named entities with general natural language types. The general natural language types comprise types of named entities across types of natural language regardless of context, for instance beyond PHI in the context of data loss prevention. Example NER models include BERT models or other natural language processing model architectures for neural networks. Depending on model architecture, there can be millions or billions of named entities. The NER model can be trained for general natural language tasks besides NER and can be modified for the task of NER.

At block 402, the trainer further trains the NER model to recognize named entities with context-based types. For instance, the context can be PHI for data loss prevention and the context-based types can comprise names, phone numbers, dates, medical terms, or other types that are encompassed by both of PII and medical terms. The trainer can modify the NER model to have output length equal to the number of context-based types and can train the NER model in additional epochs and batches of training data with backpropagation. The additional training data for the further training can comprise documents with known named entities collected across organizations and stored in a central repository. Alternatively, documents comprising sensitive data can be used in one pass for training and can be subsequently discarded to avoid leaking sensitive data by storing the documents in a repository. The training can occur until criteria are satisfied such as desired precision/recall, convergence of NER model parameters across training iterations, etc.

At block 404, the trainer preprocesses sensitive/non-sensitive documents with the NER model to output labelled named entities having context-based types. The sensitive/non-sensitive documents can comprise the documents collected across the organizations or a subset of the documents that are known to be sensitive/non-sensitive. Depending on model architecture, the NER model can generate and vectorize mean and maximal confidence values for each document corresponding to confidence that named entities of each type are correctly labelled.

At block 406, the trainer trains a random forest classifier to detect sensitive documents based on named entities with context-based types. The random forest classifier comprises a forest of trees, with each tree learning decisions at nodes and root nodes indicating sensitive or non-sensitive verdicts. The trees are trained to have non-correlated output so that the consensus verdict generated by the random forest classifier is a consensus of diverse verdicts by each tree.

Variations

The foregoing disclosure refers variously to random forest classifiers. Different types of classifiers can be implemented depending on desired interpretability of results, classification accuracy, etc. For instance, classification can be performed by employing neural network classifiers, support vector machines, etc. NER models are used for interpretability and to generate confidence values of types of named entities in documents. Other preprocessing techniques such as the word2vec algorithm can be used depending on the type of classifier implemented and desired interpretability.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. For example, the operations depicted in blocks 302, 304, 306, and 308 can be performed in parallel or concurrently across trees in the random forest classifier. The operations depicted in blocks 206, 208, 210, and 212 can be omitted or modified based on different types of preprocessing used for inputting named entities based on their types into a classifier of sensitive data. The operations at block 218 are omitted for documents with a non-sensitive data verdict for efficiency but can be instead implemented for both sensitive and non-sensitive data verdicts, for instance according to a user preference. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine-readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain, or store a program for use by or in connection with an instruction execution system, apparatus, or device. A machine-readable storage medium is not a machine-readable signal medium.

A machine-readable signal medium may include a propagated data signal with machine-readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Figure 5:
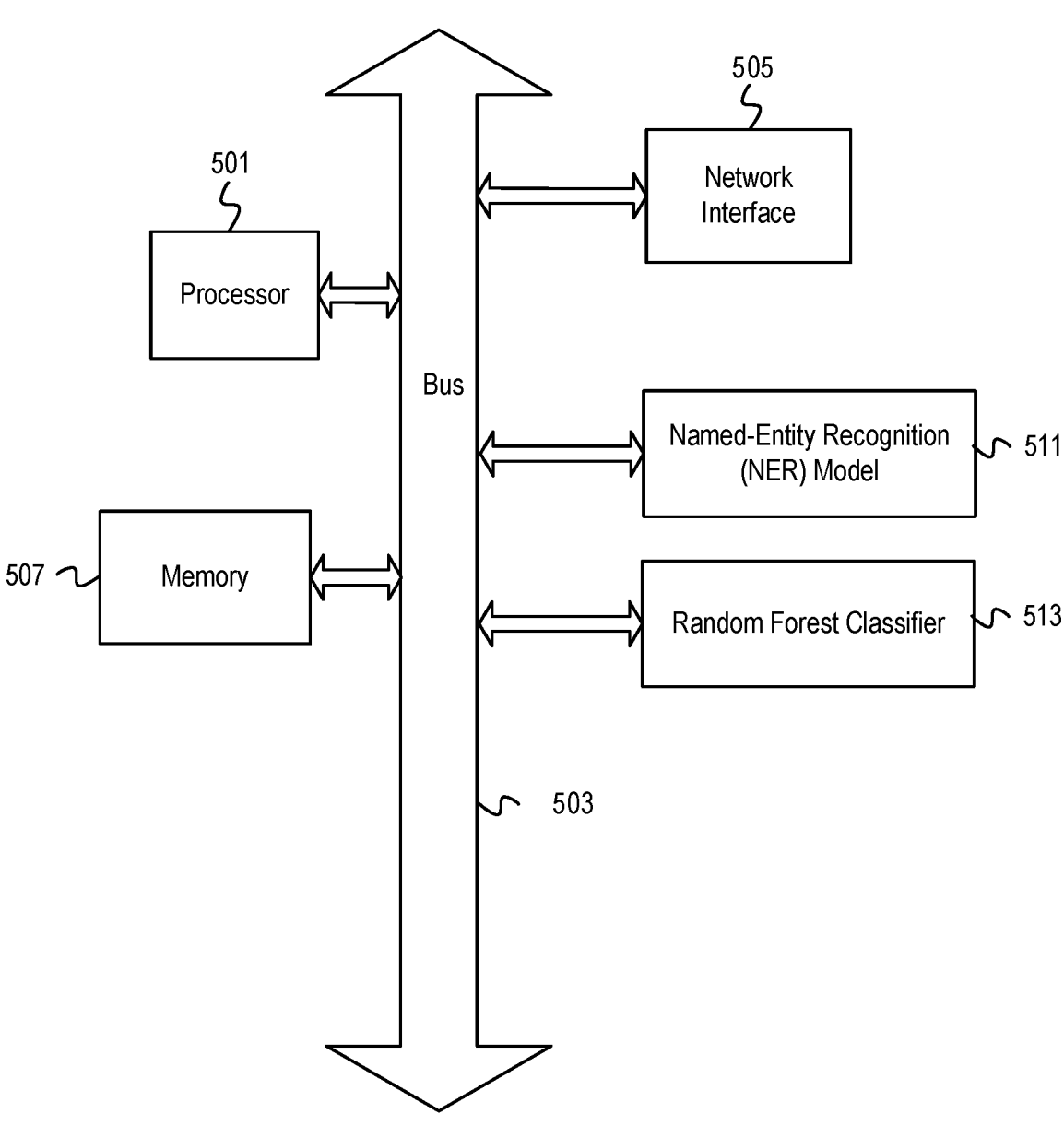
FIG. 5 depicts an example computer system with an NER model and a random forest classifier for detection of sensitive data in documents.

FIG. 5 depicts an example computer system with an NER model and a random forest classifier for detection of sensitive data in documents. The computer system includes a processor 501 (possibly including multiple processors, multiple cores, multiple nodes, and/or implementing multithreading, etc.). The computer system includes memory 507. The memory 507 may be system memory or any one or more of the above already described possible realizations of machine-readable media. The computer system also includes a bus 503 and a network interface 505. The system also includes a NER model 511 and a random forest classifier 513. The NER model 511 preprocesses truncated/tokenized documents by identifying named entities and their types and determining mean and maximal confidence values for each type of named entity in the documents. The NER model 511 is trained in the context of sensitive data to identify types of named entities that correlate with the presence of sensitive data. The random forest classifier 513 generates a verdict of sensitive data or non-sensitive data in the documents based on vectors of the confidence values for each named entity type. The random forest classifier 513 further identifies high confidence named entities that determined the verdict. Any one of the previously described functionalities may be partially (or entirely) implemented in hardware and/or on the processor 501. For example, the functionality may be implemented with an application specific integrated circuit, in logic implemented in the processor 501, in a co-processor on a peripheral device or card, etc. Further, realizations may include fewer or additional components not illustrated in FIG. 5 (e.g., video cards, audio cards, additional network interfaces, peripheral devices, etc.). The processor 501 and the network interface 505 are coupled to the bus 503. Although illustrated as being coupled to the bus 503, the memory 507 may be coupled to the processor 501.

The invention claimed is:

1. A method comprising:

determining a plurality of named entities in a document and a plurality of confidence values indicating confidence of types for each of the plurality of named entities with a named-entity recognition model, wherein the document comprises potentially sensitive data, wherein the named-entity recognition model was at least partially trained on named entities known to correspond to sensitive data;

identifying at least one of a maximal confidence value and a mean confidence value based on the plurality of confidence values for each type of entity in the plurality of named entities;

concatenating the at least one of the maximal confidence value and the mean confidence value for each type of entity to generate a vector of confidence values;

inputting the vector of confidence values and a plurality of feature values generated from the plurality of named entities into a tree-based classifier to output a verdict indicating whether the document comprises sensitive data;

determining whether the document comprises sensitive data based on the verdict, wherein the output of the tree-based classifier further indicates one or more feature importances for one or more types of the plurality of named entities in determining whether the document comprises sensitive data, wherein each of the one or more feature importances indicates relative importance of a corresponding one of the one or more types of named entities for the verdict; and based on the verdict indicating that the document comprises sensitive data, identifying, with the plurality of confidence values and the one or more feature importances, one or more of the plurality of named entities as high confidence named entities for the document comprising sensitive data.

2. The method of claim 1, wherein the named entities known to correspond to sensitive data comprise entities corresponding to personally identifiable information and medical terms, wherein the potentially sensitive data in the document comprise protected health information.

3. The method of claim 1, wherein the named-entity recognition model comprises a Bidirectional Encoder Representations from Transformers model.

4. A non-transitory machine-readable medium having program code stored thereon, the program code comprising instructions to:

input a plurality of tokens of a document into a named-entity recognition model; obtain, from output of the named-entity recognition model, a plurality of named entities and a plurality of confidence values indicating confidence in types of each of the plurality of named entities, wherein the document comprises potentially sensitive data, wherein the plurality of named entities correspond to a plurality of subsets of the document;

identify at least one of a maximal confidence value and a mean confidence value based on the plurality of confidence values for each type of entity in the plurality of named entities;

concatenate the at least one of the maximal confidence value and the mean confidence value for each type of entity to generate a vector of confidence values;

input the vector of confidence values and a plurality of feature values generated from the plurality of named entities into a tree-based classifier to output a verdict indicating whether the document comprises sensitive data;

determine whether the document comprises sensitive data based on the verdict and determine one or more feature importances for one or more types of the plurality of named entities in the determination of whether the document comprises sensitive data, wherein each of the one or more feature importances indicates relative importance of a corresponding one of the one or more types of named entities for the verdict; and based on a determination that the document comprises sensitive data indicated in output of the tree-based classifier, identify, with the plurality of confidence values and the one or more feature importances, one or more of the plurality of named entities corresponding to subsets of the document that comprise sensitive data.

5. The non-transitory machine-readable medium of claim 4, wherein the plurality of named entities comprise named entities corresponding to personally identifiable information and medical terms, wherein the potentially sensitive data in the document comprise protected health information.

6. The non-transitory machine-readable medium of claim 4, wherein the named-entity recognition model comprises a Bidirectional Encoder Representations from Transformers model.

7. An apparatus comprising:

a processor; and a machine-readable medium having instructions stored thereon that are executable by the processor to cause the apparatus to, identify a plurality of named entities in a document with a plurality of confidence values indicating confidence of types of each of the plurality of named entities based on input of a plurality of tokens of the document into a named-entity recognition model;

identify at least one of a maximal confidence value and a mean confidence value based on the plurality of confidence values for each type of entity in the plurality of named entities;

concatenate the at least one of the maximal confidence value and the mean confidence value for each type of entity to generate a vector of confidence values;

input a plurality of feature values of the of named entities and plurality the vector of confidence values into a tree-based classifier to determine whether the document comprises sensitive data and to determine one or more feature importances for one or more types of the plurality of named entities in the determination of whether the document comprises sensitive data, wherein each of the one or more feature importances indicates relative importance of a corresponding one of the one or more types of named entities for the document comprising sensitive data; and based on a determination that the document comprises sensitive data, identify, with the plurality of confidence values and the one or more feature importances, one or more of the plurality of named entities as high confidence named entities that the document comprises sensitive data.

8. The apparatus of claim 7, wherein the plurality of named entities comprise entities that correspond to personally identifiable information and medical terms, wherein the determination that the document comprises sensitive data comprises a determination that the document comprises protected health information.

9. The apparatus of claim 7 wherein the named-entity recognition model comprises a Bidirectional Encoder Representations from Transformers model.

10. The apparatus of claim 7, wherein the machine-readable medium further has stored thereon instructions executable by the processor to cause the apparatus to generate the plurality of feature values, wherein the instructions executable by the processor to cause the apparatus to generate the plurality of feature values comprise instructions to vectorize the plurality of confidence values according to corresponding ones of the plurality of named entities to generate a vector of confidence values as the plurality of feature values.

11. The apparatus of claim 7, wherein the machine-readable medium further has stored thereon instructions executable by the processor to cause the apparatus to indicate decisions at a plurality of nodes in the tree-based classifier that determined whether the document comprises sensitive data.

12. The apparatus of claim 7, wherein the instructions executable by the processor to cause the apparatus to identify the plurality of named entities and the plurality of confidence values of the named entities in the document further comprise instructions to: subdivide the document into a plurality of sub-documents; and tokenize the plurality of sub-documents to extract the plurality of tokens.

13. The method of claim 1, wherein identifying the one or more of the plurality of named entities as high confidence named entities for the document comprising sensitive data comprises, for a subset of the one or more types having top-N features importances in the one or more feature importances, identifying those of the plurality of named entities having highest confidence values in the plurality of confidence values for indicating one of the subset of the one or more types.

14. The non-transitory machine-readable medium of claim 4, wherein the program code to identify the one or more of the plurality of named entities as high confidence named entities for the document comprising sensitive data comprises instructions to, for a subset of the one or more types having top-N features importances in the one or more feature importances, identify those of the plurality of named entities having highest confidence values in the plurality of confidence values for indicating one of the subset of the one or more types.

15. The apparatus of claim 7, wherein the instructions to identify the one or more of the plurality of named entities as high confidence named entities for the document comprising sensitive data comprise instructions executable by the processor to cause the apparatus to, for a subset of the one or more types having top-N features importances in the one or more feature importances, identify those of the plurality of named entities having highest confidence values in the plurality of confidence values for indicating one of the subset of the one or more types.

16. The method of claim 1, further comprising indicating decisions at a plurality of nodes in the tree-based classifier that determined whether the document comprises sensitive data.

17. The method of claim 1, further comprising truncating and tokenizing the document prior to determining the plurality of named entities in the document and the plurality of confidence values.

18. The method of claim 1, further comprising indicating a severity level associated with the verdict.

19. The non-transitory machine-readable medium of claim 4, wherein the program code further comprises instructions to indicate decisions at a plurality of nodes in the tree-based classifier that determined whether the document comprises sensitive data.

20. The non-transitory machine-readable medium of claim 4, wherein the program code further comprises instructions to truncate and tokenize the document prior to the determination of the plurality of named entities in the document and the plurality of confidence values.

* * * * *